United States Patent [19]

Matrozza

[11] Patent Number: 4,521,434

[45] Date of Patent: Jun. 4, 1985

[54] FERMENTATION METHOD AND COMPOSITIONS INCLUDING A LACTOBACILLUS SPECIES STRAIN

[75] Inventor: Mark A. Matrozza, Sarasota, Fla.

[73] Assignee: Microlife Technics, Inc., Sarasota, Fla.

[21] Appl. No.: 423,601

[22] Filed: Sep. 27, 1982

[51] Int. Cl.$^3$ .......................... C12N 1/20; A23L 1/31
[52] U.S. Cl. ......................................... 426/59; 426/61; 426/105; 426/56; 435/253; 435/853
[58] Field of Search ...................... 435/857, 853, 253; 426/56, 57, 59, 61, 105, 55

[56] References Cited

U.S. PATENT DOCUMENTS

| | | | |
|---|---|---|---|
| 2,225,783 | 4/1939 | Jensen et al. | 426/48 |
| 2,945,766 | 4/1957 | Chaiet | 426/59 |
| 3,960,664 | 6/1976 | Olsen et al. | 435/253 |
| 3,975,545 | 8/1976 | Vedamuthu | 426/61 |
| 4,214,008 | 7/1980 | Groben et al. | 426/56 |
| 4,303,679 | 12/1981 | Raccach | 435/139 |
| 4,407,828 | 10/1983 | Raccach | 435/253 |

FOREIGN PATENT DOCUMENTS

| | | | |
|---|---|---|---|
| 590222 | 1/1960 | Canada | 426/56 |
| 849948 | 4/1958 | United Kingdom | 426/56 |

Primary Examiner—Sam Rosen
Assistant Examiner—William J. Herald
Attorney, Agent, or Firm—Ian C. McLeod

[57] ABSTRACT

Bacterial concentrates of cells of a Lactobacillus having the essential identifying characteristics of Lactobacillus sp. NRRL-B-15,036 which are useful for food fermentations are described. Lactobacillus sp. NRRL-B-15,036 ferments dextrose, but not sucrose or lactose, to produce lactic acid in the food. Lactobacillus sp. NRRL-B-15,036 is particularly useful for meat fermentations.

12 Claims, No Drawings

FERMENTATION METHOD AND COMPOSITIONS INCLUDING A LACTOBACILLUS SPECIES STRAIN

BACKGROUND OF THE INVENTION

The present invention relates to concentrates of cells of a Lactobacillus having the essential identifying characteristics of Lactobacillus sp. NRRL-B-15,036 which are useful for fermenting foods, particularly meat. The new strain ferments dextrose, but not lactose or sucrose, to produce lactic acid in the food.

PRIOR ART

The present invention relates to an improvement over the invention in U.S. Pat. No. 4,303,679 to Raccach wherein *Pediococcus pentosaceus* NRRL-B-11,465 is described for meat fermentations. The present invention also relates to an improvement over U.S. Pat. No. 3,814,817 describing *Lactobacillus plantarum* NRRL-B-5461 and over U.S. Pat. No. 3,561,977 to Rothchild et al describing *Pediococcus cerevisiae* for meat fermentations. There is a large body of prior art in this field and these patents are only representative.

Lactobacillus and Pediococcus cultures are used for meat fermentations with added dextrose to produce lactic acid. These cultures are also able to ferment available sucrose and lactose to produce lactic acid. The problem is that, when uncontrolled quantities of milk solids or other fillers containing lactose and/or sucrose are added to the meat formulation, the cultures can lower the pH to too low a level and spoil the sausage. Thus careful process control of pH is required. Certain European sausages contain significant amounts of lactose and sucrose and can particularly present a problem. This problem is aggravated with *Lactobacillus plantarum* NRRL-B-5461 and with *Pediococcus pentosaceus* NRRL-B-11,465, which are commercially available cultures, since they ferment sucrose and lactose rapidly. Another prior art problem is to provide a culture which will ferment in the meat and lower the pH at relatively low temperatures i.e. about 23.9° C. (75° F.) in a short period of time.

Until the present invention, as far as applicant is aware, the prior art has not provided bacterial cultures adapted for meat fermentations which will ferment dextrose and not sucrose and lactose to produce lactic acid and form acid rapidly at relatively low temperatures.

OBJECTS

It is therefore an object of the present invention to provide a newly isolated strain of Lactobacillus which does not have the ability to ferment lactose or sucrose and yet retains the ability to ferment dextrose to produce lactic acid in a food. It further is an object of the present invention to provide novel bacterial concentrates which maintain their capability for producing lactic acid from dextrose and will not revert to having the ability to ferment lactose and sucrose as a function of time and repropagation of the cells. These and other objects will become increasingly apparent from the following description.

GENERAL DESCRIPTION

The present invention relates to a concentrate containing a substantial proportion of cells of a Lactobacillus having the essential identifying characteristics of Lactobacillus sp. NRRL-B-15,036 which ferments dextrose to produce lactic acid and is unable to ferment lactose or sucrose to produce lactic acid, wherein the concentrate contains at least about $1 \times 10^8$ cells per ml in a nutrient medium and is in a storage stable form. The nutrient medium contains a carbohydrate source, essential minerals and a nitrogen source as is known to those skilled in the art. Various known culture preservation agents and techniques can be used to stabilize the bacterial concentrates for storage as is well known in the prior art. Glycerol is preferred for frozen concentrates as a freezing stabilizing agent. Lyophilized bacterial concentrates can also be prepared as described in U.S. Pat. No. 4,205,132. Generally the concentrates contain at least $1 \times 10^8$ cells per ml in order to provide a useful number of cells for the fermentation of the food. The cells are used in the food in concentrations between $1 \times 10^5$ to $1 \times 10^8$ cells per ml or per gram.

The present invention further relates to an improvement in the method for preparation of a fermented product by providing a culture in a food containing dextrose and then fermenting the food which comprises: providing a culture which is substantially a Lactobacillus having the essential identifying characteristics of Lactobacillus sp NRRL-B-15,036 which ferments dextrose to produce lactic acid and which does not ferment sucrose of lactose to produce lactic acid in the food and fermenting the food to produce a fermented product. The food is preferably meat.

The method and bacterial compositions can include other bacteria used in food fermentations as is known to those skilled in the art. Generally at least a substantial portion (more than about fifty percent by volume) of the concentrate will be Lactobacillus sp. NRRL-B-15,036. It would be counter-productive to use lactose and/or sucrose fermenting strains in the concentrate.

Stimulatory metal salts can be added to the Lactobacillus sp. NRRL-B-15,036 as described in U.S. Pat. No. 4,303,679 to Raccach. Manganese ion is preferred.

The following is a description of the steps in the isolation of Lactobacillus sp. NRRL-B-15,036, the preparation of bacterial concentrates and then the preparation of sausage. This strain was isolated from sausage containing sucrose and/or lactose fermenting strains as virtually the total flora (83%). It was very unexpected that this strain would be isolated.

ISOLATION OF NRRL-B-15,036

Various strains were isolated from sausage on Lactobacilli MRS$_{TM}$ agar. MRS is a selective medium designed for isolating Lactobacillus type lactic acid bacteria and is available as a powder from Difco, Detroit, Mich. A broth is prepared by adding water. MRS agar contains about 1.5% by weight of agar added to the broth. Carbohydrates are added to a fermentation broth containing the same ingredients as MRS without dextrose and with bromocresol purple added as pH indicator for determining the carbohydrate fermentation characteristics as described hereinafter. Lactobacillus sp. NRRL-B-15,036 was picked from the MRS agar and then grown in a 350 ml flask at 35° C. for 24 hours in MRS broth. The medium was then cooled to 4° C. and neutralized to a pH of 6.0. The culture was centrifuged and resuspended in about 1/10th the original volume of the culture in spent MRS broth. About 1% by volume of sterile glycerol was added along with about 18.25 percent by weight of manganese sulfate monohydrate.

The concentrated culture was then rapidly frozen on dry ice. The frozen concentrated culture contained about $83 \times 10^8$ cells per ml.

The strains were tested for lactose, sucrose and dextrose fermentation using a Mintek ® system. The isolated strains including NRRL-B-15,036 were also tested for growth at 15° C. and 45° for 64 hours with dextrose (1.0% by weight) and for growth in fermentation broth with the sucrose or lactose (1.0% by weight) using bromocresol purple as an indicator which changes from purple to yellow as the pH is lowered to about pH 5.2 due to the generation of lactic acid. The results are shown in Table I for NRRL-B-15,036 and for other strains 1 to 5 representing the predominant flora of the sausage.

TABLE I

| Isolate Number | Growth @ 45° C. | Growth @ 15° C. | Sucrose Minitek ® | Sucrose Fermentation Broth | Lactose Minitek ® | Lactose Fermentation Broth |
|---|---|---|---|---|---|---|
| NRRL-B-15036 | ± | + | − | − | − | − |
| 1 | + | + | + | N.D.* | + | N.D. |
| 2 | − | + | + | N.D. | − | N.D. |
| 3 | − | + | + | + | + | + |
| 4 | − | + | + | N.D. | − | N.D. |
| 5 | + | + | + | N.D. | + | N.D. |

*N.D. = Not Determined

It was found that even after 33 days, NRRL-B-15,036 would not ferment sucrose or lactose to produce lactic acid in a favorable growth medium. The fermentation pattern identifying characteristics of Lactobacillus sp. NRRL-B-15,036 are shown in Table II in comparison to *Lactobacillus coryniformus* subspecies *torqueus*. Strain NRRL-B-15,036 is similar to this subspecies as can be seen from Table II which is based on Bergy's manual pgs 580 and 586 but it would not be concluded that these strains were the same based upon these test results only.

TABLE II

| SUBSTRATE | POSITIVE | NEGATIVE | BBL MINITEK ® SYSTEM *Lactobacillus coryniformus* subsp. *torqueus* NRRL-B-15036 | ATCC 25600 |
|---|---|---|---|---|
| Arabinose | yel to yellow orange | Red orange | − | − |
| Cellobiose | yel to yellow orange | Red orange | − | − |
| Dextrose | yel to yellow orange | Red orange | + | + |
| Galactose | yel to yellow orange | Red orange | + | + |
| Lactose | yel to yellow orange | Red orange | − | − |
| Maltose | yel to yellow orange | Red orange | ± | + |
| Mannitol | yel to yellow orange | Red orange | − | + |
| Mannose | yel to yellow orange | Red orange | + | ± |
| Melibiose | yel to yellow orange | Red orange | − | − |
| Raffionose | yel to yellow orange | Red orange | − | − |
| Rhamnose | yel to yellow orange | Red orange | − | − |
| Salicin | yel to yellow orange | Red orange | − | − |
| Sorbitol | yel to yellow orange | Red orange | − | − |
| Sucrose | yel to yellow orange | Red orange | − | − |
| Trehalose | yel to yellow orange | Red orange | − | − |
| Xylose | yel to yellow orange | Red orange | − | − |

*Lactobacillus coryniformus* subsp *torqueus* has not previously been identified as being useful for food fermentations, particularly meat fermentations and has the essential identifying characteristics of Lactobacillus sp. NRRL-B-15,036 in that it is a Lactobacillus which will not ferment sucrose or lactose to produce lactic acid.

BACTERIAL CONCENTRATES

Bacterial concentrates of NRRL-B-15,036 were prepared as described in U.S. Pat. No. 4,303,679 to Raccach.

During growth of strain NRRL-B-15,036 the pH of medium was maintained at about 6.0 by adding ammonia until the dextrose was exhausted. The cells were concentrated by centrifugation and the resulting pellet was resuspended with supernatant medium to about 1/10 of the original volume. Glycerin was added at a concentration of 10% (W/W). Manganese sulfate monohydrate was added in the amount of 18% by weight to some samples and not others. Manganese ion contributes to the storage stability of the concentrates. The concentrate was frozen for storage and shipment prior to use and was found to be storage stable. The frozen concentrate contained about $14.5 \times 10^9$ cells per ml.

SAUSAGE PREPARATION

The following Examples show the preparation of sausage at various temperatures.

EXAMPLE 1

Pepperoni sausage was made at 23.9° C. (75° F.) using Lactobacillus sp. NRRL-B-15,036. The meat formulation was 2724 grams (6 pounds) of a mixture of 70% pork and 30% beef, coarsely chopped, to which was added: sodium chloride 81.7 grams total (3.0% by weight) including

| | |
|---|---|
| BHA | 0.82 ml (0.003% of a 10% solution) (w/v) |

| -continued | |
|---|---|
| BHT | 0.82 ml (0.003% of a 10% solution) (w/v) |
| Sodium citrate | 0.82 ml (0.003% of a 10% solution) (w/v) |
| Dextrose | 54.5 grams (2.0% by weight based on meat) |
| Pepperoni spice mix | 15.25 grams |
| sodium nitrite | 2.1 ml (200 mg/ml water solution) (156 ppm) |

In (A) of Table III the culture concentrate was added at a level of about $4 \times 10^7$ cells per gram of the meat formulation.

The inoculated meat mixture was stuffed into fibrous pepperoni casing and incubated at 23.9° C. (75° F.) internal temperature at 80% relative humidity. The results are shown in Table III.

TABLE III

| Time Hours | pH (A) |
|---|---|
| 0.0 | 5.9 |
| 17.5 | 5.44 |
| 19.0 | 5.30 |
| 20.0 | 5.13 |
| 21.0 | 5.02 |

As can be seen Lactobacillus sp. NRRL-B-15,036 is very effective in producing sausage at low temperatures.

EXAMPLE 2

To determine if manganese ion stimulates Lactobacillus sp. NRRL-B-15,036 and to determine that the manganese ion and/or nutrients in concentrated preparation of Lactobacillus sp. NRRL-B-15,036 did not stimulate normal microbial flora of meat, the meat fermentation of Example 1 was repeated at an internal meat incubation temperature of 23.9° C. (75° F.) except as follows:

In (A) of Table IV the culture concentrate was added at a level of about $4 \times 10^7$ cells per gram of meat. In (B) of Table IV manganese sulfate monohydrate was added in the amount of 18% by weight to the culture concentrate prior to freezing and the manganese ion was present in an amount of about 4 ppm of the meat formulation. In (C) of Table IV the culture concentrate was killed by autoclaving 15 min. at 121° C. and then manganese sulfate monohydrate was added in the same amount as in (B) of Table IV and manganese ion was present in an amount of about 4 ppm of the meat formulation. The results are shown in Table IV.

TABLE IV

| Time Hours | pH (A) | (B) | (C) |
|---|---|---|---|
| 0 | 5.65 | 5.65 | 5.65 |
| 16.5 | 5.50 | 5.37 | 5.64 |
| 20.5 | 5.46 | 5.29 | 5.62 |
| 24.0 | 5.16 | 5.00 | 5.60 |
| 42.5 | 4.90 | 4.50 | 5.50 |

As can be seen from Table IV, Lactobacillus sp. NRRL-B-15,036 is significantly stimulated by manganese ion in the meat. As can be seen by column (C), the manganese ion or nutrients in culture concentrate do not stimulate microbial flora normally present in meat.

It was noted that the overall speed (acid production) of cultures (A) and (B) was slower than expected (see Example 1 above). It was felt that the unusually low starting pH (5.65) of the meat may have been the reason for the slower fermentation, therefore, the experiment was repeated with cultures (A) and (B) on another batch of meat. The results are shown in Table V-a.

TABLE V-a

| Time Hours | pH (A) | (B) |
|---|---|---|
| 0 | 6.02 | 6.02 |
| 16.5 | 5.41 | 5.21 |
| 18.0 | 5.37 | 5.11 |
| 19.5 | 5.34 | 4.98 |
| 20.5 | 5.31 | 5.06 |
| 22.0 | 5.28 | 4.87 |
| 24.0 | 5.25 | 4.80 |

As can be seen from results, Lactobacillus sp. NRRL-B-15,036 is significantly stimulated by manganese ion in the meat and the higher initial pH of the meat reduced the fermentation time.

EXAMPLE 3

The meat fermentation of Example 1 was repeated at an internal meat incubation temperature of (32° C.) 90° F. except that sausage (B) was inoculated with a commercially available culture of Pediococcus pentosaceus NRRL-B-11,465. The results are shown in Table V.

TABLE V

| Time Hours | (A) | (B) |
|---|---|---|
| 0 | 5.70 | 5.70 |
| 10.5 | 5.58 | 5.32 |
| 11.5 | 5.38 | 5.10 |
| 13.5 | 5.23 | 4.77 |
| 16.0 | 5.00 | 4.55 |

As can be seen from Table V Lactobacillus sp. NRRL-B-15,036 was not as fast as Pediococcus pentosaceus NRRL-B-11,465 at 32° C.

EXAMPLE 4

The meat fermentation procedure of Example 1 was repeated at an incubation temperature of 20.6° C. (70° F.) internal meat temperature. The results are shown in Table VI.

TABLE VI

| Time Hours | (A) | (B) |
|---|---|---|
| 0 | 5.86 | 5.86 |
| 22.5 | 5.30 | 5.30 |
| 24.0 | 5.18 | 5.19 |
| 25.0 | 5.09 | 5.04 |
| 26.0 | 5.04 | 4.96 |

As can be seen from Table VI, the NRRL-B-15,036 rapidly ferments dextrose in the meat at low temperatures.

EXAMPLE 5

The procedure of Example 1 was used for making summer sausage with NRRL-B-15,036 alone (A); and compared to Pediococcus pentosaceus NRRL-B-11,465 (B) with the usual level of dextrose added. This was done to make certain there were no objectionable flavors produced by NRRL-B-15,036.

| The meat formulation was: | |
|---|---|
| Salt | 3.0% |
| Dextrose | 0.6% |
| Black Pepper | 0.11% |
| Ground Corriander | 0.11% |
| Mustard Seed | 0.055% |
| Nutmeg | 0.0275% |
| Allspice | 0.0275% |
| $NaNO_2$ | 156 ppm | in 4540 grams (10 pounds) of ground beef. Cultures were added at a level of about $4 \times 10^7$ cells per gram. The sausage was incubated at (32° C.) 90° F. at 90% relative humidity until a pH of 4.9 to 5.0 was produced. The initial meat pH was 5.80. The results are shown in Table VII.

TABLE VII

| Time Hours | (A) | (B) |
|---|---|---|
| 12 | — | 4.90 |
| 16 | 5.0 | |

There was no difference in flavor based upon triangulation taste tests by expert tasters.

It was found that the frozen bacterial concentrates were stable to storage over long periods of time (4 months) without significant loss of viability.

EXAMPLE 6

The procedure of Example 1 was repeated except lactose of sucrose was used instead of dextrose and incubation temperature was 27° C. (internal) at 80% relative humidity. The results are shown in Table VIII.

TABLE VIII

| Time Hours | (A) Dextrose only | (B) Sucrose only | (C) Lactose only |
|---|---|---|---|
| 0.0 | 5.95 | 5.95 | 5.95 |
| 16 | 5.26 | 5.66 | 5.66 |
| 24 | 5.0 | 5.65 | 5.67 |
| 48 | 4.8 | 5.60 | 5.55 |
| 67 | — | 5.56 | 5.7 |

Clearly lactose and sucrose are not fermented by the NRRL-B-15,036.

I claim:

1. A bacterial concentrate for fermenting meat to produce sausage which consists essentially of:
   (a) a biologically pure culture of cells of a Lactobacillus having the essential identification characteristics of Lactobacillus sp. NRRL-B-15,036 which cells ferment dextrose to produce lactic acid and are unsable to ferment lactose and sucrose to produce lactic acid, wherein the concentrate contains at least about $1 \times 10^8$ cells per ml in a nutrient medium and is in a storage stable form; and
   (b) a stimulatory food grade metal salt in an amount sufficient to accelerate fermentation in meat by the Lactobacillus to produce fermented sausage.

2. The concentrate of claim 1 which is frozen or lyophilized as the storage stable form.

3. The concentrate of claim 1 which contains a freezing stabilizing agent that maintains viability of the cells, and wherein the concentrate is frozen in the storage stable form.

4. The concentrate of claim 1 wherein the cells are Lactobacillus sp. NRRL-B-15,036.

5. The concentrate of claim 1 with manganese sulfate monohydrate as the metal salt.

6. The concentrate of claim 1 wherein the metal salt is a manganese salt.

7. In the method for preparation of a fermented sausage by providing a culture in meat containing dextrose and then fermenting the meat the improvement which comprises: providing a culture of a Lactobacillus having the essential identification characteristics of Lactobacillus sp. NRRL-B-15,036 which culture ferments dextrose to produce lactic acid and does not ferment sucrose of lactose to produce lactic acid and which contains a stimulatory food grade metal salt in an amount sufficient to accelerate fermentation in the meat by the Lactobacillus sp. NRRL-B-15,036 and fermenting the meat to produce the fermented sausage.

8. The method of claim 7 wherein the culture is Lactobacillus sp. NRRL-B-15,036.

9. The method of claim 7 wherein the meat contains amounts of sucrose or lactose or mixtures thereof in fillers in the meat in addition to dextrose which if fermented would reduce the pH of the fermented sausage to too low a level to be useful as a fermented sausage.

10. The method of claim 7 wherein the food contains a stimulatory amount of manganese sulfate monohydrate as the metal salt.

11. The method of claim 7 wherein the metal salt is a manganese salt.

12. The method of claim 7 wherein the fermentation is conducted at temperatures between 20.6° and 32° C.

* * * * *